Jan. 24, 1939. R. L. BYRUM Plant Pat. 312
ROSE
Filed Feb. 11, 1938
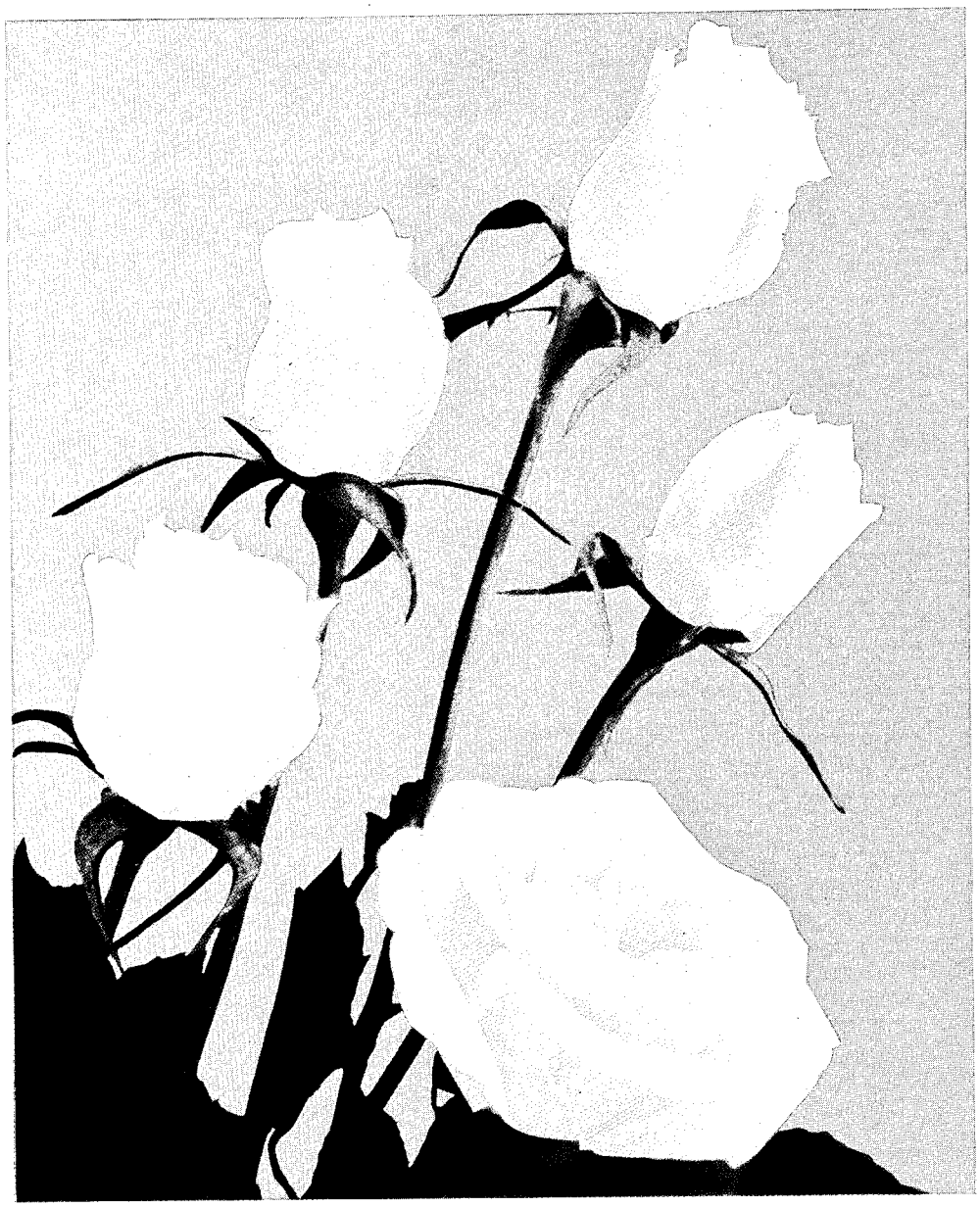
Inventor
Roy L Byrum
By Robert Robb
attorneys Patented Jan. 24, 1939

UNITED STATES PATENT OFFICE

312

ROSE

Roy L. Byrum, Richmond, Ind., assignor to Jos. H. Hill Company, Richmond, Ind.

Application February 11, 1938, Serial No. 190,113

1 Claim. (Cl. 47—61)

The present invention relates to a new and distinct variety of rose plant, the result of a definite effort to improve a known variety—"Betsy Ross"—as regards certain undesirable characteristics.

The "Betsy Ross" has a very attractive color, but being a sort of Talisman, it has a weakness of that variety in that it is inclined to be weak-stemmed.

My aim, therefore, in carrying out the present origination, was to overcome this weakness by crossing the variety with "Rapture", and in pursuing this objective, I quite unexpectedly produced a semi-miniature rose characterized as to novelty by the outstanding color of bloom for a rose of this type, hereinafter particularly described.

Additionally, this new variety is distinctive because it is very productive. It may well be compared with "Mrs. Aaron Ward", except that it is a free grower during all seasons and has a smaller bud.

In coloring, it is comparable to "Justine" (Plant Patent No. 154), but its bloom is much smaller than that of "Justine."

The original illustration shows a specimen of this new variety in substantially enlarged size and natural color, and in different stages of development from bud to full blown rose.

A sexual reproduction shows this new variety to come true to form.

The following is a detail description of the rose, all color designations being in accordance with Ridgway's color standard, except where obviously the ordinary dictionary definitions are meant:—

Parentage (seedling):

*Seed parent.*—Rapture.

*Pollen parent.*—Betsy Ross.

Classification:

*Botanic and commercial.*—Baby type Hybrid Tea.

*Flower*

Blooming habit:

(Observations were made in greenhouses of Joseph H. Hill Company, Richmond, Indiana, in November, 1937.)

Recurrent—continuous.

Bud:

*Size.*—Small. (Not as small as "Sweetheart" nor as large as "Mrs. Aaron Ward.")

*Form.*—Short, pointed.

*Color.*—When sepals first divide—citron yellow at base shading into apricot orange and coral red near top. When petals begin to unfurl:—inside—orange buff on outer edge of petals, cadmium-orange on inner part of petals; reverse side—same as tight bud. When half blown:—inside—slightly lighter shading into light orange-yellow; reverse side—remains same as in tight bud. Yellow shade predominates.

*Sepals.*—Branched; start to curl back in tight bud; fully curled when bud is half-open. Before the calyx breaks, all of the buds have foliaceous appendages on the surface of the buds. Some have much cut foliaceous parts extending beyond the tip of the bud, equal to ¼ to ½ its length. Some have entire foliaceous parts.

*Calyx.*—Shape—apple; size—small; aspect—smooth; odor when rubbed—none.

*Peduncle.*—Length—medium; aspect—smooth; color—light green; strength—slightly bending, slender.

*Opening.*—Bud opens well.

Bloom:

*Size.*—Small; average size when fully expanded—3 inches.

*Borne.*—Singly.

*Stems.*—Short, normal strength.

*Form.*—When first open—medium flat. Permanence—outer petals curl back. Retains its form to the end.

*Petalage.*—Double (full but open center); number of petals under normal conditions—45.

*Color.*—Inside of petal—light orange-yellow; reverse side—same as bud.

*Discoloration.*—Holds color well turning only slightly lighter.

Petals:

*Texture.*—Leathery.

*Appearance.*—Satiny.

*Form.*—Oval.

*Arrangement.*—Informal; petaloids in center—few.

*Persistence.*—Hang on.

*Fragrance.*—Moderate; nature—"Old Rose perfume" (Centifolia).

*Lasting quality.*—Long.

Genital organs:
*Stamens, anthers.*—Small, few; color—yellow; arrangement—mixed with petaloids.
*Stamens, filaments (threads).*—Short; color—lemon yellow and reddish brown mixed.
*Pollen.*—Gold yellow.
*Styles.*—Bunched, uneven length; short, thin.
*Stigmas.*—White.
*Ovaries.*—All enclosed in calyx.

*Plant*

Form:
Bush.
Growth:
Vigorous, sprawly.
Foliage:
5 leaflets generally, occasionally 7.
*Size.*—Medium.
*Quantity.*—Abundant.
*Color.*—New foliage: upper side—dark green; under side—light green. Old foliage: upper side—dark green; under side—light green.
*Shape.*—Oval, pointed.
*Texture.*—Smooth. Ribs and veins—ordinary.
*Edge.*—Serrated. Serration—single, small, sharp.
*Rachis.*—Color—reddish; under side—prickles.
*Stipules.*—Short.
*Disease resistance.*—Resistant.
Wood:
*New wood.*—Color—reddish brown; bark—smooth.
*Old wood.*—Color—green; bark—smooth.
Thorns:
*Quantity.*—Ordinary.
*Form.*—Narrow, flat base; medium size, straight.
*Color when young.*—Reddish.
*Position.*—Irregular.

I claim.

A new and distinct variety of baby-type Hybrid Tea rose, characterized as to novelty by its semi-miniature size, its great productivity and the unusual coloring of its flower in a rose of this type, substantially as shown and described.

ROY L. BYRUM.